US00PP14647P29

(12) United States Plant Patent

Fischer-Töhl

(10) Patent No.: US PP14,647 P2
(45) Date of Patent: Mar. 30, 2004

(54) GERANIUM PLANT NAMED 'SIL ONNO'

(50) Latin Name: *Pelargonium×hortorum*
Varietal Denomination: Sil Onno

(75) Inventor: Ilse Fischer-Töhl, Kirchlintein (DE)

(73) Assignee: Wolfgang Silze, Weener (DE)

( * ) Notice: Subject to any disclaimer, the term of this patent is extended or adjusted under 35 U.S.C. 154(b) by 0 days.

(21) Appl. No.: 10/361,924

(22) Filed: Feb. 10, 2003

(51) Int. Cl.[7] ..... A01H 5/00
(52) U.S. Cl. ..... Plt./329
(58) Field of Search ..... Plt./329, 330, 324

(56) References Cited

U.S. PATENT DOCUMENTS

PP8,088 P * 1/1993 Heidgen ..... Plt./330
PP8,100 P * 1/1993 Heidgen ..... Plt./330
PP9,305 P * 9/1995 Stoots ..... Plt./330
PP9,746 P * 12/1996 Dummen ..... Plt./329
PP10,395 P * 5/1998 Trees ..... Plt./329
PP11,678 P * 12/2000 Trees ..... Plt./329
PP12,455 P2 * 3/2002 Trees ..... Plt./330
PP12,457 P2 * 3/2002 Trees ..... Plt./324
PP12,476 P2 * 3/2002 Trees ..... Plt./330
PP13,944 P2 * 7/2003 Trees ..... Plt./330

OTHER PUBLICATIONS

UPOV ROM GTITM computer database, GTI Jouve Retrieval Software 2003/04 Citation for 'Sil Onno'.*

* cited by examiner

*Primary Examiner*—Bruce R. Campell
*Assistant Examiner*—W C Haas
(74) *Attorney, Agent, or Firm*—C. A. Whealy

(57) ABSTRACT

A new and distinct cultivar of Geranium plant named 'Sil Onno', characterized by its upright and mounded growth habit; dark green-colored leaves; and red purple-colored semi-double flowers.

2 Drawing Sheets

Botanical classification/cultivar designation: *Pelargonium×hortorum* cultivar Sil Onno.

BACKGROUND OF THE INVENTION

The present invention relates to a new and distinct cultivar of Geranium plant, botanically known as *Pelargonium×hortorum*, and hereinafter referred to by the name 'Sil Onno'.

The new Geranium is a product of a planned breeding program conducted by the Inventor in Weener, Germany. The objective of the breeding program is to develop new upright and mounded Geranium cultivars that flower uniformly and have attractive flower and foliage coloration.

The new Geranium originated from a cross-pollination made by the Inventor in 1998 of the *Pelargonium×hortorum* cultivar Silfra, not patented, as the female, or seed, parent with the *Pelargonium×hortorum* cultivar SEL Lucky, not patented, as the male, or pollen, parent. The cultivar Sil Onno was discovered and selected by the Inventor as a flowering plant within the progeny from this cross-pollination in a controlled environment in Weener, Germany.

Asexual reproduction of the new cultivar by terminal cuttings taken at Weener, Germany, since September, 1998 has shown that the unique features of this new Geranium are stable and reproduced true to type in successive generations of asexual reproduction.

SUMMARY OF THE INVENTION

The following traits have been repeatedly observed and are determined to be the unique characteristics of 'Sil Onno'. These characteristics in combination distinguish 'Sil Onno' as a new and distinct Geranium cultivar:

1. Upright and mounded growth habit.
2. Dark green-colored leaves.
3. Red purple-colored semi-double flowers.

Plants of the new Geranium differ primarily from plants of the parents in leaf coloration, flower form and flower coloration.

The new Geranium can be compared to the cultivar, Purple Rose, disclosed in U.S. Plant Pat. No. 10,395. However, in side-by-side comparisons conducted in West Chicago, Ill., plants of the new Geranium differed from plants of the cultivar Purple Rose in the following characteristics:

1. Plants of the new Geranium had smaller leaves with shorter petioles than plants of the cultivar Purple Rose.
2. Plants of the new Geranium had larger inflorescences than plants of the cultivar Purple Rose.
3. Plants of the new Geranium had more petals per flower than plants of the cultivar Purple Rose.
4. Plants of the new Geranium had shorter peduncles than plants of the cultivar Purple Rose.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a side perspective view of a typical flowering plant of 'Sil Onno'.

The photograph on the second sheet is a close-up view of a typical flower of 'Sil Onno'. Flower and foliage colors in the photographs may differ slightly from the color values cited in the detailed botanical description which accurately describe the colors of the new Geraniurm.

DETAILED BOTANICAL DESCRIPTION

The cultivar Sil Onno has not been observed under all possible environmental conditions. The phenotype may vary somewhat with variations in environment such as temperature and light intensity, without, however, any variance in genotype. The aforementioned photographs and following observations and measurements describe plants grown in West Chicago, Ill., under commercial practice in a polycarbonate-covered greenhouse with day temperatures ranging from 18 to 24° C., night temperatures ranging from 14 to 18° C. and light levels ranging from 3,500 to 6,000 foot-candles. Plants used for the photographs and description were about 10 weeks from planting rooted cuttings in 10-cm containers. In the following description, color references are made to The Royal Horticultural Society Colour Chart, 2001 Edition, except where general terms of ordinary dictionary significance are used.

Botanical classification: *Pelargonium×hortorum* cultivar Sil Onno.

Parentage:

*Female parent.*—*Pelargonium×hortorum* cultivar Silfra, not patented.

*Male parent.*—*Pelargonium×hortorum* cultivar SEL Lucky, not patented.

Propagation:

*Type cutting.*—Terminal cuttings.

*Time to initiate roots.*—About 7 days at 18° C.

*Time to develop roots.*—About 21 days at 18° C.

*Root description.*—Fibrous, freely branching.

Plant description:

*General appearance.*—Upright and mounded growth habit. Appropriate for 10-cm and larger containers.

*Growth and branching habit.*—Moderately vigorous freely basal branching with about three lateral branches at the base. Pinching, that is, removal of terminal apices, will enhance lateral branch development.

*Plant height* (*to top of foliage*).—About 10.5 cm.

*Plant height* (*to top of inflorescences*).—About 19.6 cm.

*Plant width.*—About 18 cm.

*Lateral branches.*—Length: About 5.6 cm. Internode length: About 6.1 mm. Texture: Pubescent. Color: 144A.

*Foliage description.*—Arrangement: Opposite, simple. Quantity of leaves per lateral branch: About 12. Length: About 4.2 cm. Width: About 6.9 cm. Shape: Reniform. Apex: Rounded. Base: Cordate. Margin: Crenate. Venation: Palmate. Texture, upper and lower surfaces: Velvety; pubescent. Color: Developing and fully expanded foliage, upper surface: Darker than 147A; venation, 145A; no zonation pattern. Developing and fully expanded foliage, lower surface: 147B; venation, 146C. Petiole: Length: About 4.3 cm. Diameter: About 3 mm. Texture, upper and lower surfaces: Pubescent. Color, upper and lower surfaces: 146A.

Flower description:

*Flower arrangement and type.*—Semi-double rounded flowers arranged in hemispherical umbels arising from apical leaf axils. Umbels displayed above the foliage. At fall flowering, usually about five opened and developing umbels per plant. Umbels persistent. Flowers not fragrant.

*Flowering season.*—Year-round under greenhouse conditions. In the garden, flowering is continuous from spring until fall. Plants start flowering about eight weeks after planting.

*Flower longevity.*—Flowers last about 14 to 18 days on the plant.

*Umbels.*—Diameter: About 10.1 cm. Height: About 5.5 cm. Number of flowers per umbel: About 10. Flower diameter: About 5 cm. Flower depth (height): About 1.9 cm.

*Flower buds.*—Length: About 1.4 cm. Diameter: About 9 mm. Shape: Ovoid. Color: Brighter than 53B.

*Petals/petaloids.*—Quantity: About eight or nine petals and about one or two petaloids per flower. Petaloids variable in size and shape. Arrangement: Imbricate. Petal length: Upper petals: About 2.9 cm. Lower petals: About 2.6 cm. Petal width: Upper petals: About 2.1 cm. Lower petals: About 2.2 cm. Petal shape: Obovate. Petal/petaloid apex: Rounded, obtuse. Petal/petaloid base: Attenuate. Petal/petaloid margin: Entire. Petal/petaloid texture, upper and lower surfaces: Smooth. Petal/petaloid aspect: Slightly cupped. Petal/petaloid color: When opening and fully opened, upper surface: Towards margin, darker than N66A; center, N66A; towards base, 44B; venation, 60A; color becoming closer to 64B with development. When opening and fully opened, lower surface: Towards margin, N57B; towards base, 43B; venation similar to petal/petaloid color.

*Sepals.*—Quantity: Five per flower; not imbricate on open flowers. Length: About 1.1 cm. Width: About 4 mm. Shape: Ensiform to lanceolate. Apex: Acuminate. Margin: Entire. Texture, upper surface: Glabrous. Texture, lower surface: Pilose. Color, upper and lower surfaces: 143C overlain with 183A.

*Peduncle* (*umbel stem*).—Length: About 10.3 cm. Angle: Erect. Strength: Strong. Texture: Densely pubescent. Color: 144A overlain with 183B.

*Pedicel* (*individual flower stem*).—Length: About 3.2 cm. Angle: Erect. Strength: Strong. Texture: Moderately pubescent. Color: 143D overlain with 183A.

*Reproductive organs.*—Androecium: Anther quantity: About ten per flower. Anther length: About 2 mm. Anther color: 61A. Pollen amount: Moderate. Pollen color: 170B. Gynoecium: Pistil quantity: One per flower. Pistil length: About 1 cm. Stigma shape: Five or six-parted, star-shaped. Stigma color: 61A. Style length: About 3 mm. Style color: 61A. Ovary color: 144A.

*Seed/fruit.*—Seed and fruit production has not been observed.

Disease/pest resistance: Resistance to pathogens and pests common to Pelargonium has not been observed.

It is claimed:

1. A new and distinct cultivar of Geranium plant named 'Sil Onno', as herein illustrated and described.

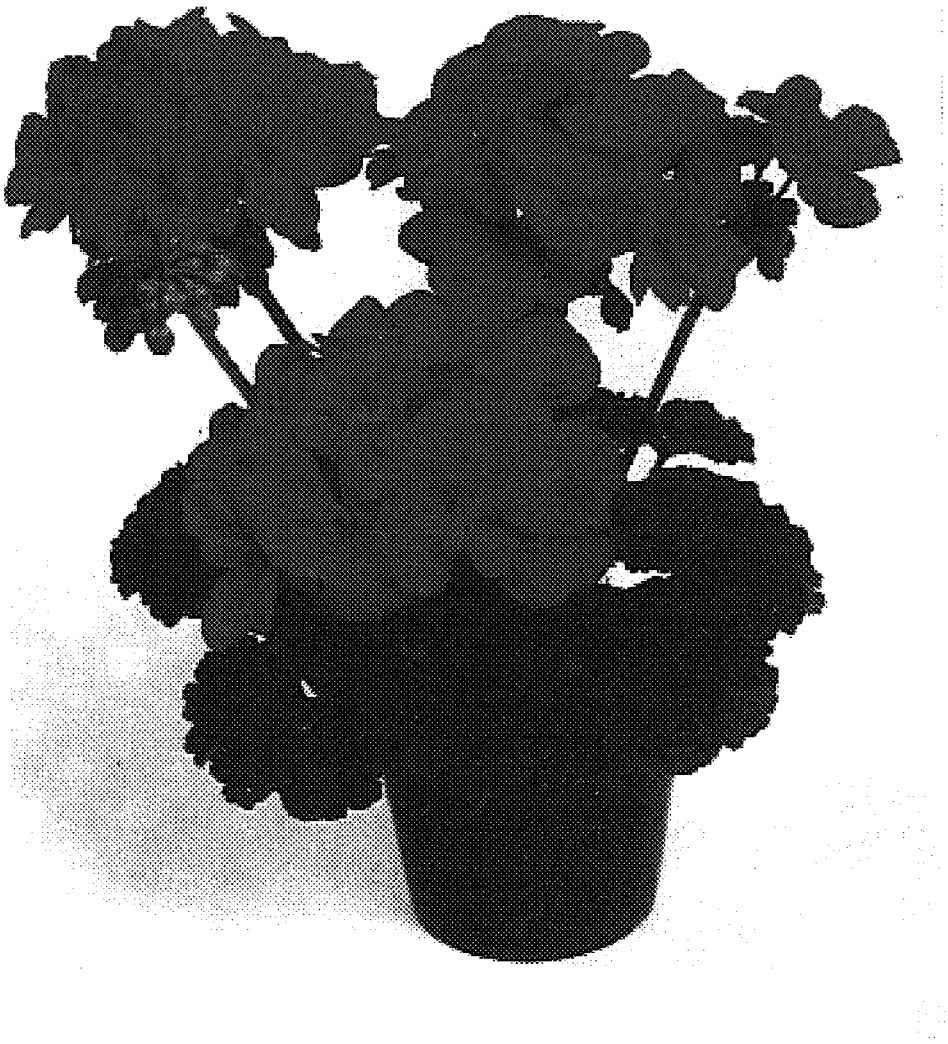

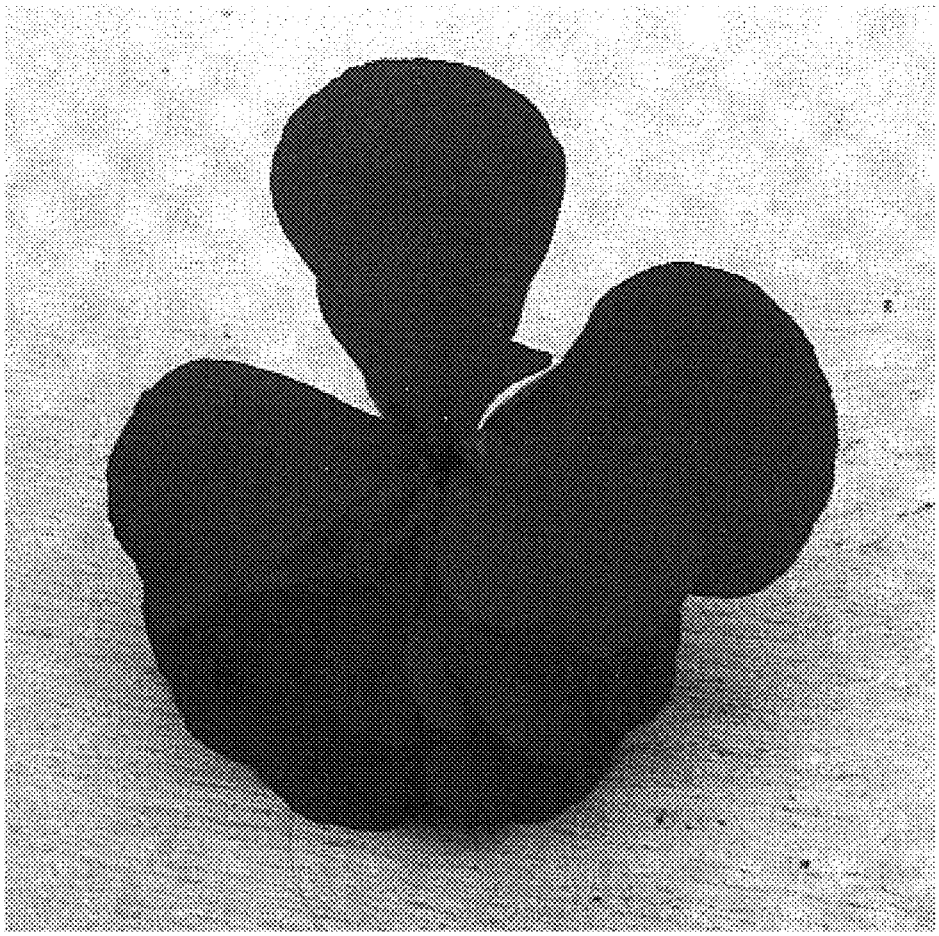

* * * * *